US010561462B2

(12) United States Patent
Dalal et al.

(10) Patent No.: US 10,561,462 B2
(45) Date of Patent: Feb. 18, 2020

(54) SYSTEM AND METHOD FOR TEMPERATURE FEEDBACK FOR ADAPTIVE RADIO FREQUENCY ABLATION (75) Inventors: Sandeep Dalal, Eindhoven (NL); Jochen Kruecker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 748 days.

(21) Appl. No.: 13/825,353

(22) PCT Filed: Sep. 22, 2011

(86) PCT No.: PCT/IB2011/054163
§ 371 (c)(1),
(2), (4) Date: Mar. 21, 2013

(87) PCT Pub. No.: WO2012/042443
PCT Pub. Date: Apr. 5, 2012

(65) Prior Publication Data
US 2013/0184700 A1 Jul. 18, 2013

Related U.S. Application Data (60) Provisional application No. 61/387,549, filed on Sep. 29, 2010.

(51) Int. Cl.
*A61B 18/12* (2006.01)
*A61B 18/18* (2006.01)
(Continued)

(52) U.S. Cl.
CPC .......... *A61B 18/18* (2013.01); *A61B 18/1206* (2013.01); *A61B 90/37* (2016.02);
(Continued)

(58) Field of Classification Search
CPC . A61B 18/10; A61B 18/1206; A61B 18/1233; A61B 2018/00791; A61B 2018/00797
(Continued)

(56) References Cited

U.S. PATENT DOCUMENTS 5,800,484 A 9/1998 Gough et al.
5,810,804 A 9/1998 Gough et al.
(Continued)

FOREIGN PATENT DOCUMENTS

EP 1554986 7/2005
WO 2010096419 A2 8/2010

OTHER PUBLICATIONS

C.D. Anderson et al., "Real-Time Spectroscopic Assessment of thermal Damage: Implications for Radiofrequency Ablation", Journal of Gastrointestinal Surgery, vol. 8, No. 6, 2004, pp. 660-669.
(Continued)

*Primary Examiner* — Michael F Peffley
*Assistant Examiner* — Bo Ouyang (57) ABSTRACT A system and method for ablation include ablating (508) a target volume using an ablation probe and collecting (510) temperature information around the target volume. A shape of an ablation volume is determined (512) based upon the temperature information. The shape is displayed (520) on a display relative to an image of the target volume.

16 Claims, 6 Drawing Sheets (51) Int. Cl.
    *A61B 18/00* (2006.01)
    *A61B 34/10* (2016.01)
    *A61B 90/00* (2016.01)
    *A61B 34/20* (2016.01)

(52) U.S. Cl.
    CPC ............ *A61B 2018/00577* (2013.01); *A61B 2018/00797* (2013.01); *A61B 2034/104* (2016.02); *A61B 2034/2051* (2016.02); *A61B 2090/378* (2016.02)

(58) Field of Classification Search
    USPC .................................. 606/42; 607/101, 102
    See application file for complete search history.

(56) References Cited

U.S. PATENT DOCUMENTS

| | | | |
|---|---|---|---|
| 5,833,688 A * | 11/1998 | Sieben ............... | A61B 18/1492 606/15 |
| 6,241,725 B1 * | 6/2001 | Cosman ........................ | 606/41 |
| 6,575,969 B1 | 6/2003 | Rittman, III et al. | |
| 7,160,296 B2 | 1/2007 | Pearson et al. | |
| 7,344,533 B2 * | 3/2008 | Pearson et al. ................. | 606/41 |
| 7,419,487 B2 | 9/2008 | Johnson et al. | |
| 8,346,370 B2 | 1/2013 | Haley et al. | |
| 8,540,710 B2 | 9/2013 | Johnson et al. | |
| 9,747,684 B2 | 8/2017 | Trovato et al. | |
| 2002/0077627 A1 | 6/2002 | Johnson et al. | |
| 2006/0155267 A1 * | 7/2006 | Berzak ................... | A61B 18/02 606/20 |
| 2006/0200121 A1 | 9/2006 | Mowery | |
| 2009/0118613 A1 * | 5/2009 | Krugman et al. ............ | 600/431 |
| 2010/0063496 A1 | 3/2010 | Trovato et al. | |
| 2010/0185087 A1 * | 7/2010 | Nields .................... | A61B 18/18 600/439 |
| 2011/0306969 A1 * | 12/2011 | Coe et al. ....................... | 606/41 |

OTHER PUBLICATIONS

Y.H. Mah et al., "Quantification of Ablation Size in Ex Vivo Bovine liver using cool-Tip Radiofrequency Ablation System", IFMBE proceedings, 4th Kuala Lampur International Conference on Biomedical Engineering 2008, vol. 21, Part 3 (8), pp. 615-618.

B.J. Wood et al., "Technologies for Guidance of Radiofrequency Ablation in the Multimodality Interventional Suite of the Future", J. Fasc. Intern. Radiol. Jan. 2007; 18(1 Pt. 1): pp. 9-24.

* cited by examiner

SYSTEM AND METHOD FOR TEMPERATURE FEEDBACK FOR ADAPTIVE RADIO FREQUENCY ABLATION

This disclosure relates to medical arts, and more particularly to a system and method for employing temperature feedback for planning ablation procedures.

Ablation procedures such as radio frequency ablation (RFA) have been increasingly performed in recent years as an alternative to more invasive surgical procedures. During RFA, an electrode with un-insulated tip is inserted into a tumor or lesion to be ablated under ultrasound, computed tomography (CT) or magnetic resonance imaging (MRI) guidance. When the electrode is placed, a radio frequency current is applied to the tip which creates tissue heating and cell death above 60° Celsius.

To destroy tumors that are larger than the volume around the needle tip, the needle tip needs to be repeatedly repositioned to ablate different parts of the tumor, with the treated volumes partly overlapping each other. This process needs to be repeated until the entire tumor is covered by the set of ablations, also referred to as a "composite ablation".

Currently, these composite ablations are performed with basic imaging guidance from ultrasound (US) or CT, but usually without navigation assistance and without quantitative or computerized planning. The results of the procedure largely depend on the intuition and experience of the physician. The process of composite ablation planning and execution is difficult, and it has been pointed out that full coverage of a planning target volume (PTV) with (smaller) individual ablations generally requires a surprisingly large number of ablations.

Thus, there is no guarantee that a "mentally planned" composite ablation actually fully covers the PTV, or that it covers the PTV in an optimal fashion, i.e. with the minimum number of ablations (each ablation taking between 12 and 20 minutes). Also, due to inaccuracies in executing or placing the ablation probes according to a "mental plan", the PTV coverage actually achieved may be insufficient to eradicate the tumor, leading to local tumor recurrence.

RFA planning systems have been developed to address problems in computing an optimal number (typically as few as possible) and placing multiple overlapping ablations to cover the entire tumor volume plus an added safety margin of 0.5-1.0 cm around the tumor (this combined volume is termed as the Planning Target Volume (PTV)) without causing excessive damage to healthy tissue surrounding the tumor. Planning systems enable the clinician to visualize and quantitatively assess the impact of the planned ablations on tumor coverage.

Navigation systems employing a form of spatial tracking (e.g. electromagnetic/optical means) of the RFA electrode tip and the ultrasound transducer probe position and orientation have also been developed to improve conventional image guidance by, e.g., referencing the RFA electrode position directly to three-dimensional coordinates of a pre-acquired medical image (e.g., CT scan). However, these navigation systems exist independently of planning systems and are thus not useful in executing or iteratively improving the procedure plan.

A size or shape of an ablation actually achieved during a radio frequency ablation (RFA) procedure is affected by the presence of blood flow in vessels adjacent to a tumor volume. A cooling effect of blood flow near the ablation is termed as a "heat sink" effect. The heat sink impact is to change the overall shape of the ablation, and may cause incomplete treatment. This could possibly lead to a recurrence of the tumor. To ensure complete treatment, the achieved ablation shapes need to cover the entire PTV. Residual (unablated) PTV regions are usually discovered by performing contrast-CT or contrast-US scans during the procedure. However, use of contrast agents may not be indicated or poorly tolerated by some patients. Therefore, a meaningful indicator of achieved ablation shape/size is needed to ensure complete treatment that does not involve use of contrast or extra CT scans.

In accordance with the present principles, systems and methods for ablation are provided, which include ablating a target using an ablation probe and collecting temperature information around the target. A shape of an ablation volume is determined based upon the temperature information. The shape is displayed on a display relative to an image of the target.

In one embodiment, an ablation system includes an ablation probe and a radio frequency generator coupled to the probe to energize the probe and configured to collect temperature information from tissue surrounding a target volume. A marker is mounted on the probe to provide a reference position for an imaging modality so that locations for which the temperature information is collected can be determined. A module is configured to determine a shape of an ablation volume based upon the temperature information and display the shape on a display relative to an image of the target volume.

In another embodiment, a workstation includes a processor and memory coupled to the processor. The memory is configured to store and execute, with the processor, a module to determine a shape of an ablation volume based upon temperature information measured during an ablation process and display the shape on a display relative to an image of the target volume.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

The present disclosure describes systems and methods for planning optimal tumor coverage with multiple accurately placed radio frequency ablations (RFA). An ablation volume created with commercially available RFA electrodes is nominally defined by the manufacturer as spherical or ellipsoidal in shape with a certain diameter(s). However, in real procedures, the achieved ablation shape/size varies from patient to patient and depends on the heat sink effect of the tumor's local environment, e.g., proximity to blood vessels, size or blood flow rate in these vessels, etc.

In accordance with the present principles, RFA electrodes may embed temperature sensors to monitor an achieved temperature during the ablation. This temperature information is used by an RF generator that drives the electrode to adjust the ablation process. The temperature is also monitored qualitatively by a clinician to judge safety, effectiveness, completion, etc. of the ablation process. In one embodiment, the temperature measurements are integrated in a quantitative manner to estimate achieved ablation shape/size at the completion of a single ablation. This information is used to compute a residual tumor volume permitting an updated plan to compute the necessary number and placement of ablations to optimally cover a residual tumor. In accordance with the present principles, temperature measurements from the RFA electrode are employed to estimate the achieved ablation size/shape to be used as a feedback system.

RFA probes may include temperature sensors embedded in the needle electrode tip (or in individual tines) to sense the temperature of the tissue being ablated. In the case of a multi-tine RFA probe (e.g., Starburst™ XL/XLi RFA electrodes from Angiodynamics™), the RF generator driving the RFA probe, uses criteria of an ablation being complete. One such criterion is the measurement of an average temperature across the multiple sensors being greater than a user-specified target temperature for a pre-specified amount of time.

In one particularly useful embodiment, a temperature measured on each tine at the end of an ablation may be used to sense any loss of heat due to the presence of blood flow in nearby blood vessels. A tine near a large blood vessel will likely record a lower achieved temperature in the tissue as compared to a tine farther away from any blood vessel. This temperature measurement may be displayed continuously on the RF generator supplying power to the RFA probe inserted into the tissue during the ablation. The temperature measurement is advantageously employed during the ablation or at the completion of the ablation to estimate the likely change in the shape from the nominal or pre-determined shape/size specified by a manufacturer for the specific RFA electrode driven by the corresponding RF generator.

It should be understood that the present invention will be described in terms of medical instruments and in particular ablation instruments; however, the teachings of the present invention are much broader and are applicable to any instruments employed in destroying tissue using heat or heat generating techniques or cooling techniques, such as cryo ablation and the like. In particular, the present principles are applicable to procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Figure 1:
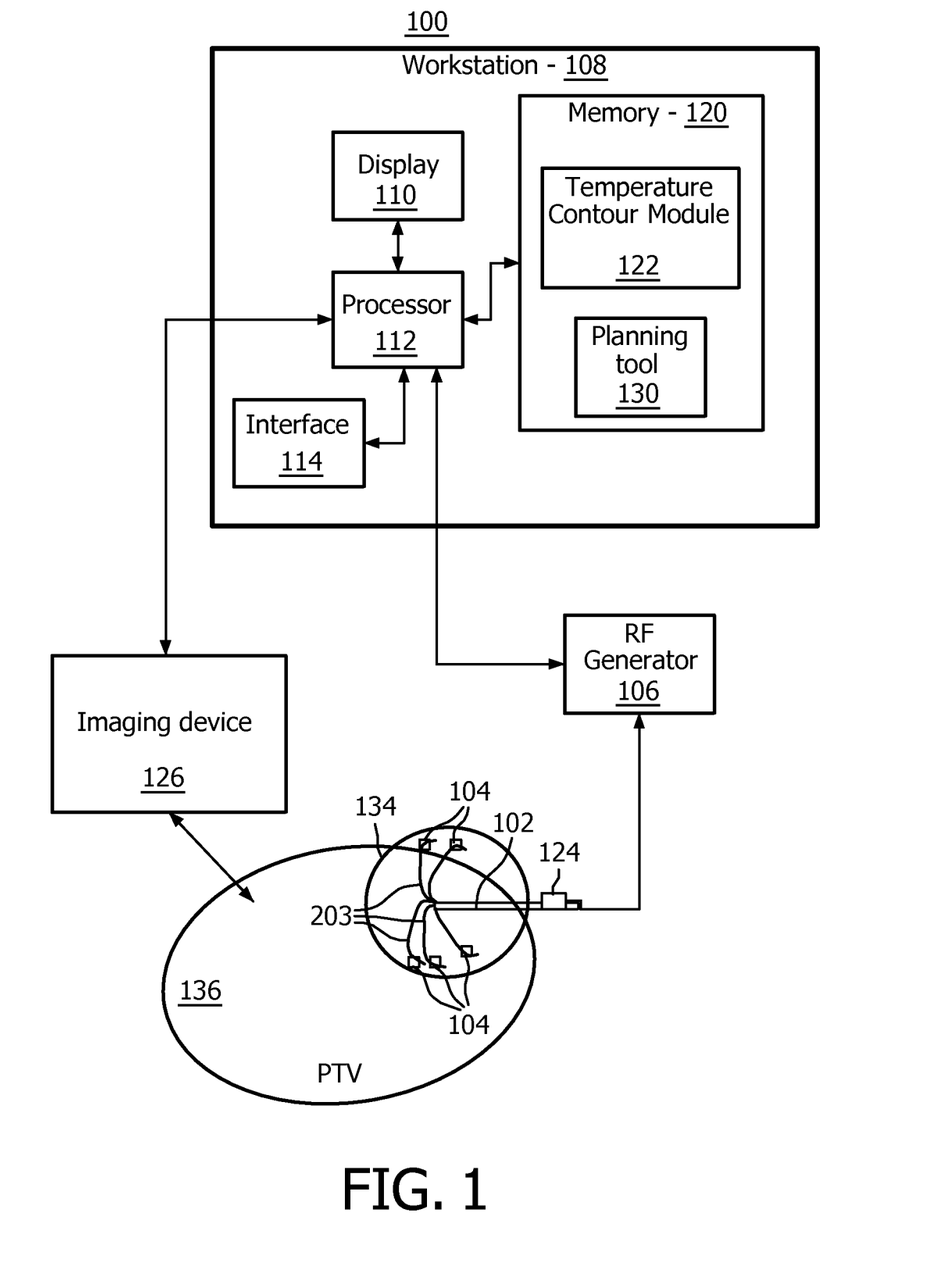
FIG. 1 is a block diagram showing an ablation system which employs temperature feedback in accordance with one illustrative embodiment.

Referring now to the drawings in which like numerals represent the same or similar elements and initially to FIG. 1, a system 100 is illustratively shown which enables quantitative estimation of ablation shapes and sizes using temperature feedback. The system 100 includes a radio frequency ablation (RFA) probe 102 (e.g., a single tine or a multi-tine probe) with one or more embedded temperature sensors 104 (e.g., mounted along a single tine or on multiple tines). The temperature sensors 104 are preferably mounted on or in the RFA probe 102, although other ways of measuring temperature may be employed. For example, a separate device (e.g., a needle) may be inserted in the area to measure tissue temperature.

Other devices may include catheters or devices with sensors or imaging equipment to provide temperature measurements through contact or indirect measurement (e.g., thermal imaging). In one embodiment, the probe 102 may include only a single temperature sensor (e.g., in single-needle or triple-cluster probes). If the RFA probe 102 does not have embedded temperature sensors 104, fine-gauge needles with embedded temperature sensors 104 at their tip inserted in the vicinity of a target volume may be employed to determine the temperature distribution around an ablation zone.

An RF generator 106 communicates temperature data to a workstation 108 that provides planning/navigation/ablation feedback information to the user using, e.g., a display 110. The workstation 108 may include a computer processor 112, the display 110, a user interface 114 (e.g., mouse, keyboard, etc.) and memory 120 for storing data and software. Memory 120 includes software, which may include a temperature contour module 122 configured to employ the temperature feedback information to determine a most likely shape/size of an ablation volume surrounding an ablation site.

The module 122 determines a position of the temperature sensors 104 relative to a marker 124 fixed elsewhere on the probe 102. In this way, the temperature sensor positions are known relative to the marker 124 for a given measurement. The module 122 is capable of determining the position of the temperature sensors 104 as well as the marker 124 on the probe 102 as deployed during a specific ablation treatment by use of a medical imaging modality 126 (e.g., CT, Ultrasound). The imaging modality 126 includes a scanner or other imaging device (e.g., CT, US, X-ray, etc.). Ultrasound or (rotational) X-ray imaging may be employed (e.g., instead of CT) for the scans. If a multi-tined probe 102 is employed, the tines need not be extracted individually from the CT data, if the position of the temperature sensors are known relative to the marker 124, e.g., using EM tracking.

The marker 124 may alternately include a spatial tracking system/device that can be used to determine RFA probe position relative to a medical image (instead of using a CT image of the RFA probe). For example, a 6 degree-of-freedom electromagnetic (EM) tracking sensor can be placed on the RFA probe as the marker 124. The position of the temperature sensors 104 on RFA tines 203 can then be identified (one-time calibration) relative to this fixed EM tracked sensor. This permits the position of the temperature sensors 104 to be known during an ablation and permits the temperature data to be spatially registered accurately on any modality image that is acquired with a spatial registration to the EM tracking sensor.

The module 122 collects continuous temperature data from the RF generator 106 and displays the temperature data overlaid on the imaging scan showing the RFA probe 102 inserted into the PTV. The overlaid temperature data is shown at spatially correct positions using the marker deployed on the RFA probe. The temperature data can be converted into estimated ablation diameters along radial directions on parallel equatorial planes to represent the achieved ablation shape. The temperature data at specific points in the region may be displayed, and the ablation shape can also be overlaid on the CT scan and the PTV to display the volume of the ablated voxels inside the PTV. A RF ablation feedback method may subtract the ablated voxels inside the PTV from the entire PTV to compute a residual PTV. The residual PTV represents the untreated zone and is the input to an updated RFA plan computation. In addition, temperature feedback or computed ablation volumes may employ other imaging information, e.g., real-time ultrasound echogenicity, to display the ablated zone.

Based on temperature feedback, the module 122 is capable of computing an achieved ablation shape or treatment region based on the temperature data. Using a mapped volume or other image of an internal region of a subject, the temperature data can be visualized on the display 110 by overlaying a temperature distribution over a planning target volume (PTV) for a lesion or tumor. Using the temperature data, the module 122 computes a transformation to the shape and size of an ablation with the RFA probe 102. This transformed ablation shape can be overlaid on the PTV so that the clinician or physician can visualize a more accurate version of an affected region.

Module 122 further provides that a residual PTV is computed and visualized by subtracting all ablated voxels inside the transformed ablation shape that are also inside the original PTV. The computation of the residual PTV during an ablation procedure is performed by using the transformed ablation shape for feedback.

An RFA planning tool 130 may be stored in memory 120 and compute an optimal number and placement of ablations to cover the entire PTV or the residual PTV as ablations are performed during the procedure. We assume the manufacturer-specified ideal size and shape of the ablation for planning a RFA procedure. This may be achieved under the assumption of unperfused and perfectly homogeneous tissue; but this shape is unrealistic for ablations in perfused non-homogeneous tissue. Blood flow in nearby vessels alters the shape of the ablation by cooling the ablation zone locally. If the highest temperature measured by a sensor 104 in a certain tine (for a multi-tined probe 102) is lower than 50° C. then it is unlikely that the tissue around the sensed area has been ablated. System 100 enables correlation of temperature readings from each sensor 104 by geometrically registering the 3D positions of the sensors to the tissue regions where the probe is inserted. This permits temperature maps to be determined and overlaid on ablation shapes, and consequently, estimates likely changes in the shape from a pre-determined shape specified by the manufacturer.

Using temperature as a means of feedback permits a physician to employ the probe 102 or ablation device itself with its embedded temperature sensors 104 to estimate an ablation shape 134. This permits a visualization of actual temperatures overlaid on the anatomical features in an image or images around the ablation zone. An ablation radius is estimated for each temperature measurement, and a 3-dimensional volume corresponding to that transformed ablation shape is computed. Contrast ultrasound or contrast-CT scans are not necessary to estimate a residual PTV 136 as this can be handled using the temperature feedback such that the impact of heat loss along certain directions of the ablation is estimated, and a computation to estimate the ablation shape based on temperature feedback from the RFA probe 102 is provided.

Figure 2:
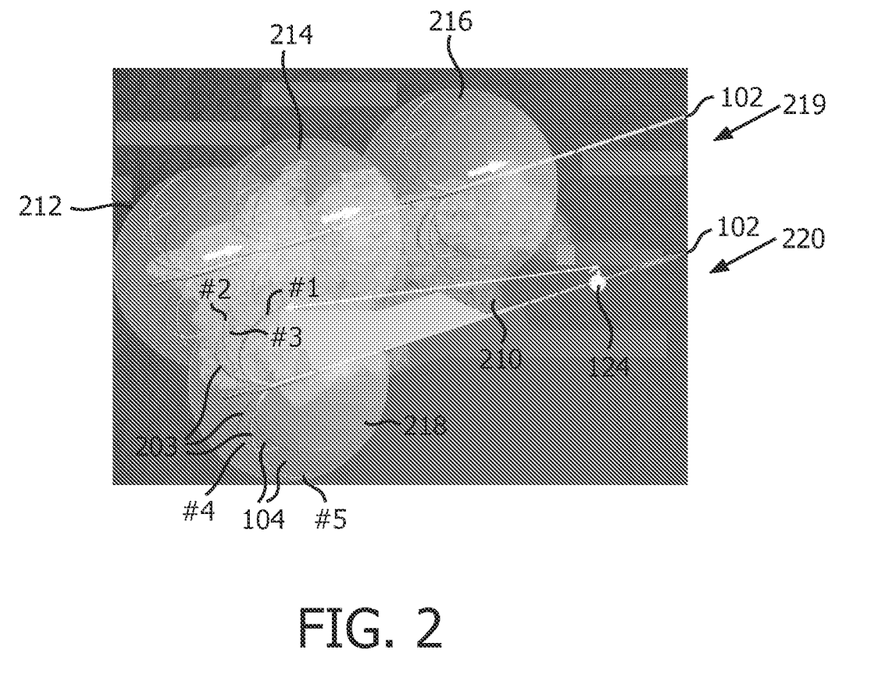
FIG. 2 is a diagram showing an ablation procedure with multiple ablations with an RFA probe deployed with a marker aligned to a specific tine in accordance with one illustrative embodiment.

Referring to FIG. 2 with continued reference to FIG. 1, a multi-tined probe 102 is illustratively shown. Tines 203 of probe 102 may include temperature sensors 104. Temperature data is provided from an RF generator 106 to an external computer (workstation 108) performing the RFA procedure planning, navigation and feedback. This data can be provided via any appropriate method, e.g. USB, serial port, parallel port, network interface, etc. The multi-tine RFA probe 102 may be cylindrically symmetric in shape. Temperature sensors 104 are arranged on some of these tines but we do not know a-priori which sensor is indicative of the temperature on a specific tine 203. The marker 124 is placed on the RFA probe 102 that accurately aligns the temperature from a sensor to a specific tine. For example, if the multi-tine probe has five temperature sensors, marked as #1, 2, 3, 4, and 5, then we establish a convention that the marker 124 is co-oriented with the tine 203 that records the temperature reading on sensor #1. This marker 124 should be made of a material that is easily distinguishable in, e.g., a CT scan since it should be correlated with the deployed tine (this is easily visible under CT) and thereby the temperature measurement along the direction of that specific tine 203.

The marker 124 should be firmly attached to the RFA probe 102 without interfering with the therapeutic function of the RFA probe 102. A possible location could be a probe handle or on the insulated shaft nearest to the probe handle. Marker 124 is shown in FIG. 2 to be aligned with the tine 203 marked with #1.

The ablation probe 102, which is driven by the generator 106, is specified by the probe manufacturer to produce a spheroid or ellipsoid-shaped ablation with specified ablation diameters. An ellipsoid-shaped ablation has three independent diameters. A spheroid-shaped ablation has three diameters of which two are equal. In practice, cylindrically symmetric ablations are specified as spheroids. The ablation diameter perpendicular to the axis (handle-to-needle-tip) of the RFA probe 102 is an equatorial diameter, the ablation diameter parallel to the axis of the RFA probe 102 is a polar diameter.

In FIG. 2, a first pass 219 has an ablation probe 102 advanced distally into tissue of a lesion 210 and an ablation procedure results in a thermal ablation 212. Then, the probe is retracted proximally to further perform additional ablations 214 and 216. The procedure continues with a new pass 220, resulting in ablation 218. This continues until the lesion 210 is completely treated. The ablated tissue preferably extends beyond the lesion 210, but without unnecessarily destroying healthy tissue.

For each ablation, the RF generator 106 is usually programmed with an ablation termination method, e.g., one that lets the user specify the time needed for the average temperature recorded by the probes to exceed a certain value before the ablation is considered completed. Once the specified condition is achieved, the RF generator 106 shuts off power to the RFA probe 102. Under ideal conditions, if all temperature sensors 104 recorded a uniform increase in temperature from the start of the ablation to the end of the ablation, and if a final temperature recorded on all symmetrically disposed sensors 104 were equal, then we expect the equatorial and polar diameters of the achieved ablation to be optimal. These optimal diameters could be assumed to be equal to the manufacturer-specified ablation diameters, or they could be obtained from a prior calibration study or via simulation studies using finite-element-models.

For a single temperature sensor probe 102, the temperature data may be used to modify a single diameter of the ablated zone in the equatorial plane directly. This maintains the overall ablation shape as a spheroid but takes the impact of micro-perfusion in the tissue that affects the overall ablation size. If temperature is measured by a plurality of needles or other devices independent of the probe 102, the ablation shape can be inferred by estimating the actual temperature recorded during an ablation versus ideal temperatures in a calibration study or the like (as in, e.g., FIG. 3). The distance from the ablation electrode tip to the temperature sensors will influence the temperature.

A calibration study may be performed on, e.g., homogeneous unperfused tissue (i.e., all tines 203 expected to record almost equal temperatures) in which actual ablation diameters from histology/post-ablation contrast CT or MR scans are correlated to temperature measurements recorded at the end of the ablation just-prior to the generator shutting off power to mark the ablation as completed. This calibration study would record the actual ablation diameters as a function of average temperature recorded on the tines.

Figure 3:
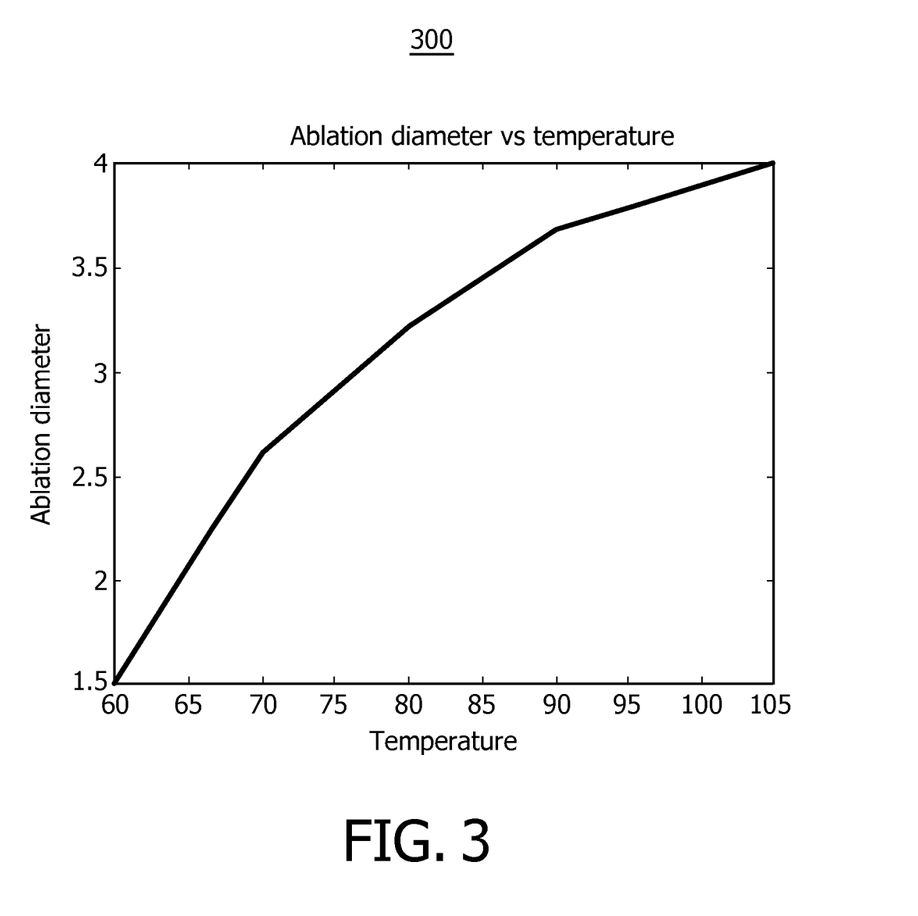
FIG. 3 is a plot showing a relationship between ablation diameter and temperature to be employed in computing new ablation shapes in accordance with one illustrative embodiment.

Referring to FIG. 3, a plot 300 of a relationship between ablation diameter versus temperature is illustratively shown. The plot 300 correlates temperatures measured during an ablation with the geometry of the ablation shape. Such a function can be programmed into module 122 to result in a graphical display showing ablated regions in a CT or MRI scan. Other plots with different temperature profiles or related to other conditions (e.g., asymmetric temperature distributions) may be employed to adjust the displayed shapes and sizes.

Other information (e.g., clinical condition of patient, overall perfusion, etc.), or models (e.g., finite element modeling of heat transfer given segmented vessels near the RFA probe) can also be employed to determine the relationship of how the ablation is likely modified in the presence of blood flow. For example, finite element modeling (FEM) in the presence of cooling effects of blood vessels at a known distance, orientation, flow, etc. from the ablation enables computation of temperatures at the positions of the temperature sensors.

Knowing the asymmetry in the temperature data from the RFA probe 102, the blood flow in the vicinity can be inferred and the ablation shape can be modulated using the FEM model relationship instead of a relationship relating ablation diameter to temperature derived from the calibration study of FIG. 3.

Referring again to FIG. 2 with continued reference to FIG. 1, CT scans may be used to confirm the position of the RFA probe 102 as it is advanced to the precise location approved by the clinician (or interventional radiologist). The clinician may also use the RFA planning tool 130 to compute and visualize the placement of a set of overlapping ablations as in FIG. 2. A CT scan shows the final position of the deployed RFA probe 102 along with each of the exposed tines including the marker 124. The marker's orientation would be aligned with a specific temperature sensor on a tine 203 (assume, e.g., the sensor numbered #1), and the other temperature sensors 104 on different tines, which are in known geometric positions relative to the sensor #1. The tines 203 can be segmented or traced on the CT scan. A known spatial location of the temperature sensor 104 on each tine corresponds to a specific voxel in the tissue. This location may be known from the design of the RFA probe, e.g., the temperature sensor 104 may be embedded at the tine tip, or at a known distance from the tine tip. The geometric registration permits the present system/method to overlay specific temperature values communicated from the RF generator 106 to be overlaid on specific tissue points in the CT scan.

Once the temperatures from sensors 104 are geometrically registered to specific voxels in the tissue, we then estimate the impact on the ablation shape. If all the tines are uniformly deployed in the tissue, the temperature sensors 104 (typically symmetrically disposed on each tine 203) will lie on a unique three-dimensional plane. Therefore, the voxels corresponding to these sensed temperature points will lie on a geometric plane parallel to the equatorial plane of the ideal ablation spheroid.

Figure 4:
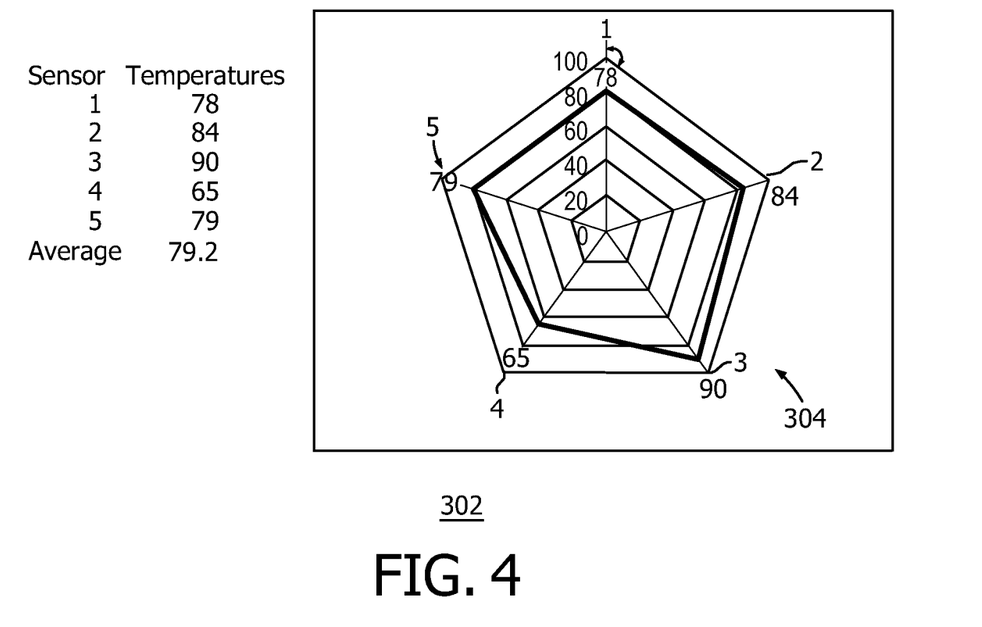
FIG. 4 is a chart and plot showing measured temperatures for each of five temperature sensors embedded in a RFA probe interpolated to form a curve in accordance with one illustrative embodiment.

Referring to FIG. 4, a chart 302 shows an example of temperature data plot 304 recorded from five sensor positions #1-5 at some point in the ablation. This example shows different individual temperatures ranging from 65° C.-90° C., with an average temperature of 79.2° C. The RF generator (106) has been programmed to terminate the ablation when the average temperature has been higher than 60° C. for more than 5 minutes. This is considered to be a successful ablation. However, the temperature on tine #3 (5 o'clock position) is 90° C. versus tine #4 (7 o'clock position), which is only 65° C. This implies that there is likely to be some non-uniformity in the ablation shape.

Figure 5A:
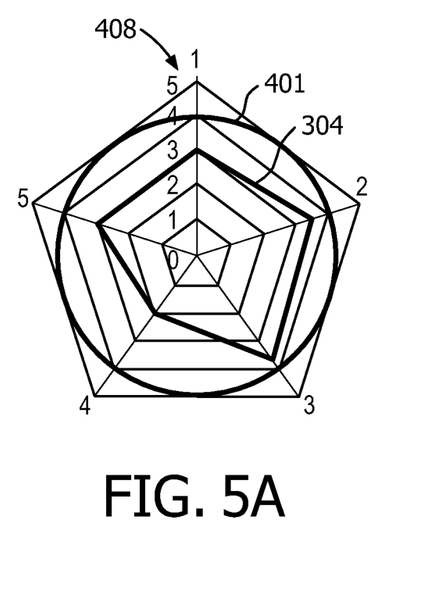
FIG. 5A is a plot showing the curve of FIG. 4 and a circle contour showing equal temperatures on each sensor conforming to the nominal or expected shape of the ablation.
Figure 5B:
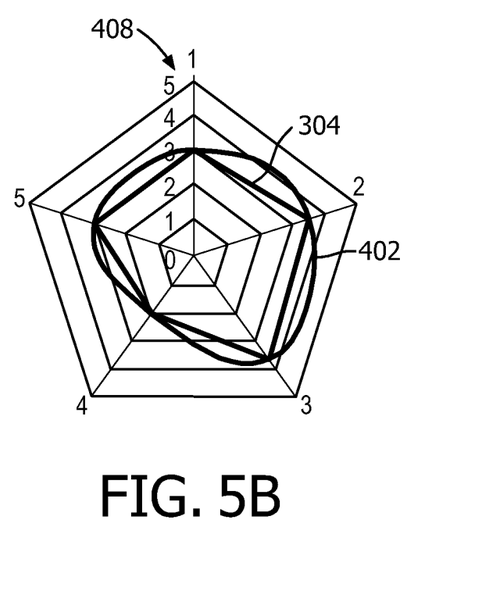
FIG. 5B is a plot showing the curve of FIG. 4 and an adjusted contour computed by splines for adjusting an ablation shape in accordance with the present principles.

Using the function of FIG. 3, for example, we can now estimate a possible ablation shape for this temperature distribution using interpolation techniques (e.g., linear, spline, etc). For example, if a uniform maximum ablation diameter of 4.0 cm were to be achieved for a temperature of 105° C. (according to FIG. 3), the ablation diameter would be a uniform 4 cm in all directions. FIG. 5A shows a uniform circle 401 indicating the equatorial diameter of 4 cm of a spheroidal ablation at the 105° C. temperature. However, for the temperature distribution of FIG. 4 (plot 304), the ablation diameters would be transformed as shown in FIG. 5B. FIG. 5B shows a spline interpolation 402 as well as the linear interpolation 304. In FIGS. 5A and 5B, a vertical line scale 408 shows an achieved diameter from 0 to 5 cm, and sensor numbers 1-5 are distributed outside the polygons. If a sensor measures 105 degrees C. (from FIG. 3) the diameter of the ablation shape is at 4 cm. This is performed for all temperature measurements to relate temperature to diameter of the ablation volume.

The ablation shape in this plane is no longer a circle, but a generalized 2-dimensional closed contour (402). This contour 402 reflects the ablation shape on a single plane parallel to the equatorial plane of the ablation. Along parallel planes moving away from the equatorial plane, we use a proportionately scaled down version of this transformed shape. The proportionality constant is simply the diameter of the original uniform circle on that plane relative to the diameter of the circle on the equatorial plane. This produces a deformed ablation shape along the polar axis of the ablation spheroid.

Mathematically the steps, which may be performed using module 122 for determining the transformed ablation shape, are as follows:

1. An ablation spheroid has circular contours in each equatorial plane (the x-y plane). The axis of the needle represents the z coordinate. The diameter of the circles varies as a function of the polar coordinate (z). Assume $D(z)$ is the function representing the diameter of the uniform ablation (circular contour) at the value z (polar value). The equatorial plane of the ablation is at a fixed value of $z=z_0$.

2. The transformed contour $f(x, y, z=z_0)$ is computed on the equatorial plane using the observed temperature distribution (FIG. 4) and the measured calibration (FIG. 3) relating ablation diameter to observed temperature.

3. For all planes parallel to the equatorial plane, the transformed contour points on $f(x, y, z=z_0+d)$ relative to the center of the circle are proportionately scaled by the value $D(z=z_0+d)/D(z=z_0)$. This creates a distorted ablation shape which is proportionately scaled down on all equatorial planes compared to the uniform ablation spheroid.

These multiple contours produce a 3-dimensional ablation shape reflecting the impact of the measured temperature along the sensor positions. The residual PTV is what remains of the original PTV after subtracting all the voxels included in this 3-dimensional ablation shape.

In accordance with one embodiment, a single-tine sensor (See e.g., FIG. 7) may include a needle or catheter with one or more temperature sensors disposed thereon. If one or more temperature sensors are located along the needle's polar axis instead of in the equatorial plane, the individual temperature measurements could be used to proportionately scale the nominal diameter of the standard ablation shape in the equatorial plane in which the sensor is located. For a spheroid shaped standard ablation, the ablation contour in the equatorial plane (that includes the location of the temperature sensor) is a circle with a nominal diameter $D(z=z1)$. FIG. 3 establishes the relationship between the measured temperature for a given sensor location and the achieved ablation diameter in that equatorial plane. The actual temperature measured for the given sensor location determines the achieved ablation diameter for the plane of the sensor. Achieved ablation diameters for other planes are scaled in proportion to the achieved ablation diameter in the plane of the sensor.

Figure 6:
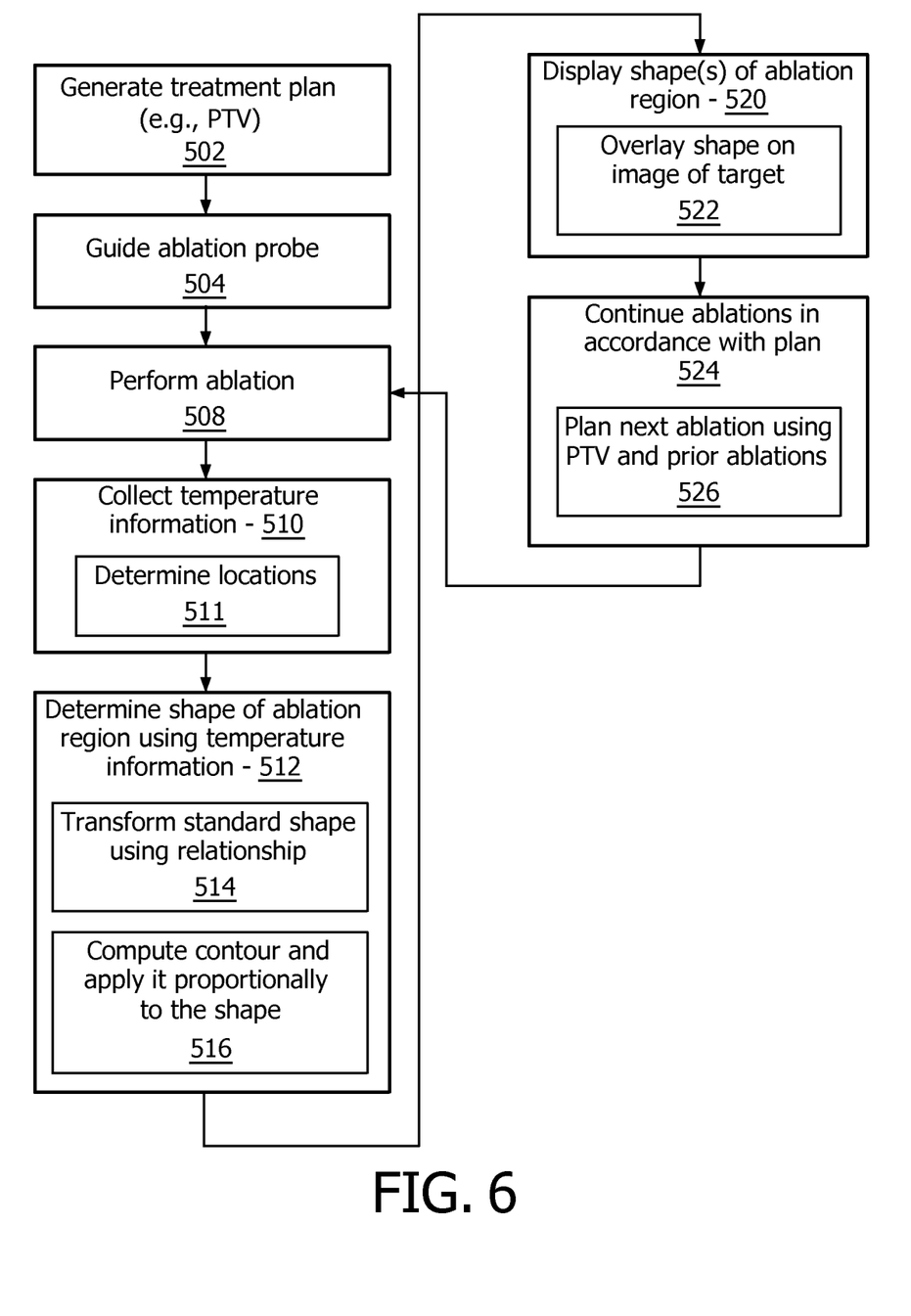
FIG. 6 is a flow diagram showing an ablation method which employs temperature feedback in accordance with one illustrative embodiment.

Referring to FIG. 6, a method for ablating tissue using temperature information as feedback is shown in accordance with one embodiment. In block 502, an initial treatment plan is optionally developed for treating target tissue. This may include defining a planning treatment volume (PTV) in a subject. In block 504, an ablation probe is guided to the target tissue in a subject.

In block 508, at a selected position, the ablation probe is energized to destroy tissue, preferably in accordance with the treatment plan. In block 510, during the ablation (and after the ablation) temperature is monitored at or near the target tissue. Temperature information is collected around the target using temperature sensors that may be mounted on the probe or separately placed (e.g., needles, etc.). If the temperature sensors are separately placed they may be inserted close to the target to measure temperature around the ablation volume. The temperature information may also be measured using temperature sensors on a multi-tined ablation probe. In block 511, temperature information is collected for known locations. The locations may be determined in a plurality of ways, e.g., a marker or a tracker may be employed to identify positions of temperature sensors and provide spatial registration to the image acquired with an imaging modality, which registers the sensor positions to spatial locations in the tissue being treated.

In block 512, a shape of an ablation volume is determined based upon the temperature information. The temperature information is employed to determine whether the ablation shape needs to be modified as a result of distortions to the temperature distribution. These distortions may be as a result of blood flow, the subject's anatomy or other influences. The shape of the ablation volume may be determined by transforming a standard shape ablation volume in accordance with a relationship between ablation geometry versus temperature in block 514. The relationship may include a calibration study, a model, such as a finite element model, etc. In one embodiment, the standard shape is transformed or adjusted by computing an ablation contour using interpolation in accordance with the relationship, and proportionally adjusting the shape in other areas to provide the shape of the ablation in block 516.

In block 520, the shape with its distortions, etc. is displayed on a display relative to an image of the target. In this way, a more accurate depiction of the ablated area can be seen, which reduces the chance that untreated tumors or other tissue will remain after the procedure. The displayed image may include the shape of the ablation volume overlaid on a three-dimensional image of the subject in block 522. In this way, the ablated portions of the target can be visualized relative to the image, the planning target volume (PTV), other ablations, etc.

Figure 7:
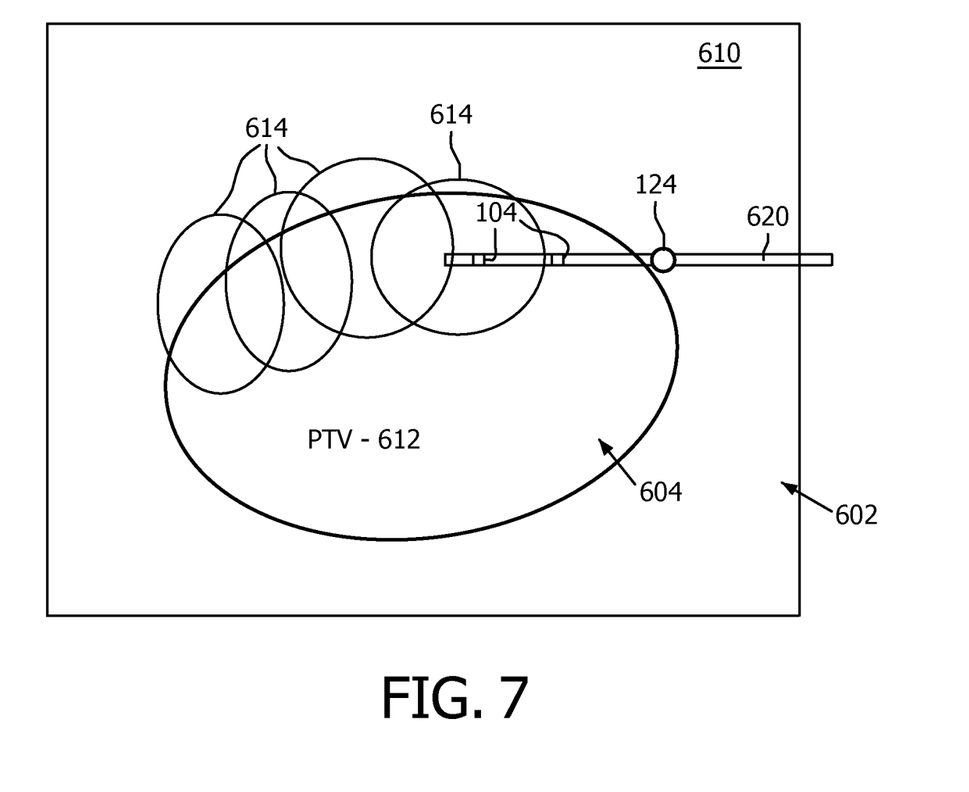
FIG. 7 is a diagram illustratively showing an image with a planning treatment volume (PTV) and having multiple ablation shapes overlaid on a target region such that further ablation planning can be performed in accordance with the present principles.

In block 524, subsequent ablations may be continued and displayed in accordance with the PTV. The PTV is compared, preferably visually, with a plurality of transformed ablation shapes as estimated during the procedure. FIG. 7 shows an illustrative example of such a display. The plurality of transformed ablation shapes defines the residual PTV. A plan with additional ablations is computed to cover the residual PTV to ensure treatment of the original PTV in its entirety, in block 526.

Referring to FIG. 7, an illustrative display image 602 is depicted. The image 602 includes a CT scan or other image of a target region 604 inside a patient 610. In this embodiment, a single-tined device 620 is employed. The single-tined device 620 may include one or more sensors 104 along its length. The device may be a needle, a catheter or other device. A marker 124 may also be employed to assist in locating the device 620. A PTV region 612 is generated and depicted in the image 602. In addition, ablation volumes 614, as modified by temperature feedback, are depicted with the PTV to promote a highly accurate surgical procedure in accordance with the present principles.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for temperature feedback for adaptive radio frequency ablation (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system, comprising:
an ablation probe which includes at least one temperature sensor that is configured to collect temperature information from tissue surrounding a target volume;
a radio frequency generator coupled to the probe to energize the probe;
a marker mounted on the probe that provides a reference position for an imaging modality so that locations for the at least one temperature sensor which collects the temperature information can be determined; and
a module stored in a non-transitory memory that includes processor executable instructions that when executed by a processor configures the processor to perform a method comprising acts of:
receiving a shape of an ablation volume verses temperature for unperfused homogeneous tissue for the ablation probe;
receiving the collected temperature information from the at least one temperature sensor;
transforming the shape of the ablation volume based upon the collected temperature information, a relationship between ablation diameter versus temperature and the locations of the at least one temperature sensor determined based on the position of the marker, wherein the transforming is performed iteratively starting with an equatorial plane of the at least one temperature sensor and extends outward in all directions in planes parallel to an equatorial plane of the at least one temperature sensor; and
displaying the transformed shape on a display relative to an image of the target volume.

2. The system as recited in claim 1, wherein the probe includes a multi-tined ablation probe having temperature sensors on a plurality of tines for collecting the temperature information, and wherein transforming the shape of the ablation volume comprises acts of determining a temperature distribution from the temperature sensors and adjusting the shape of the ablation volume based on the temperature distribution.

3. The system as recited in claim 1, wherein the shape variations from the predetermined standard shape of the ablation volume include ablation contours computed using interpolation in accordance with the relationship to proportionally adjust a shape of the ablation and wherein the collected temperature information measured for a given temperature sensor location of the at least one temperature sensor determines an ablation diameter for an equatorial plane of the given temperature sensor and ablation diameters for planes parallel to the equatorial plane are scaled in proportion to the ablation diameter in the equatorial plane of the given temperature sensor.

4. The system as recited in claim 1, wherein the processor is further configured by the module to perform an act of overlaying the shape of the ablation volume in a three-dimensional image of the target volume.

5. The system as recited in claim 1, wherein the system is configured to allow a user to visually compare a planning target volume with a plurality of displayed ablation shapes to plan a next ablation using the target volume and the plurality of displayed ablation shapes to ensure treatment of the planning target volume in its entirety.

6. A workstation, comprising:
a processor;
a non-transitory memory coupled to the processor, the memory being configured to store a module that includes processor executable instructions that when executed by the processor configures the processor to perform acts of:
receiving a shape of an ablation volume verses temperature for unperfused homogeneous tissue for a given ablation probe;
receiving temperature information for tissue surrounding a target volume that is collected by at least one temperature sensor mounted on, or integrated in, the given ablation probe;
transforming the shape of the ablation volume based upon the temperature information and a relationship between ablation diameter versus temperature, wherein the transforming is performed iteratively starting with an equatorial plane of the at least one temperature sensor and extends outward in all directions in planes parallel to an equatorial plane of the at least one temperature sensor; and
displaying the transformed shape on a display relative to an image of the target volume.

7. The workstation as recited in claim 6, wherein the temperature information is gathered by a multi-tined ablation probe having temperature sensors on a plurality of tines and wherein transforming the shape of the ablation volume comprises acts of determining a temperature distribution from the temperature sensors and adjusting the shape of the ablation volume based on the temperature distribution.

8. The workstation as recited in claim 6, wherein the transformed shape includes ablation contours computed using interpolation in accordance with the relationship to proportionally adjust the shape of the ablation volume and wherein the collected temperature information measured for a given temperature sensor location of the at least one temperature sensor determines an ablation diameter for an equatorial plane of the given temperature sensor and ablation diameters for planes parallel to the equatorial plane are scaled in proportion to the ablation diameter in the equatorial plane of the given temperature sensor.

9. The workstation as recited in claim 6, wherein the module is configured to overlay the transformed shape of the ablation volume in a three-dimensional image of the target volume.

10. The workstation as recited in claim 6, wherein the workstation is configured to allow a user to visually compare a planning target volume with a plurality of displayed ablation shapes to plan a next ablation using the target volume and the plurality of displayed ablation shapes to ensure treatment of the planning target volume in its entirety.

11. A method, comprising:
  ablating a target volume using an ablation probe having a marker mounted on the probe that is configured to provide a reference position;
  collecting temperature information around the target volume by at least one temperature sensor that is mounted on, or integrated in, the ablation probe;
  determining locations of the at least one temperature sensor based on a position of the marker;
  receiving a shape of an ablation volume verses temperature for unperfused homogeneous tissue for the ablation probe;
  transforming the shape of the ablation volume based upon the temperature information, a relationship between ablation diameter versus temperature and the location of the at least one temperature sensor determined based on the position of the marker, wherein the transforming is performed iteratively starting with an equatorial plane of the at least one temperature sensor and extends outward in all directions in planes parallel to an equatorial plane of the at least one temperature sensor; and
  displaying the transformed shape on a display relative to an image of the target volume.

12. The method as recited in claim 11, further comprising computing an ablation contour using interpolation in accordance with the relationship and proportionally adjusting the shape in other areas to provide the transformed shape of the ablation volume, wherein the collected temperature information measured for a given temperature sensor location of the at least one temperature sensor determines an ablation diameter for an equatorial plane of the given temperature sensor and ablation diameters for planes parallel to the equatorial plane are scaled in proportion to the ablation diameter in the equatorial plane of the given temperature sensor.

13. The method as recited in claim 11, wherein displaying the transformed shape on a display relative to an image of the target volume includes overlaying the transformed shape in a three-dimensional image of the subject.

14. The method as recited in claim 11, further comprising continuing ablations in accordance with a planning target volume (PTV).

15. The method as recited in claim 14, wherein planning target volume is visually compared with a plurality of displayed ablation shapes.

16. The method as recited in claim 11, further comprising developing a treatment plan for treating target tissue.

* * * * *